US00PP17052P3

(12) United States Plant Patent
Kapiteijn

(10) Patent No.: US PP17,052 P3
(45) Date of Patent: Aug. 22, 2006

(54) ***ZANTEDESCHIA* PLANT NAMED 'CAPTAIN RENO'**

(50) Latin Name: *Zantedeschia Spreng.*
Varietal Denomination: Captain Reno

(75) Inventor: Antonius S. J. Kapiteijn, Anna Paulowna (NL)

(73) Assignee: Kapiteijn Breeding BV, Anna Paulowna (NL)

( * ) Notice: Subject to any disclaimer, the term of this patent is extended or adjusted under 35 U.S.C. 154(b) by 33 days.

(21) Appl. No.: 11/145,086

(22) Filed: Jun. 4, 2005

(65) Prior Publication Data

US 2005/0278816 P1 Dec. 15, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

PP15,294 P2 * 11/2004 Warren et al. ..... Plt./263
PP15,808 P2 * 6/2005 Warren et al. ..... Plt./263

OTHER PUBLICATIONS

UPOV ROM GTITM Computer Database, GTI Jouve Retrieval Software 2005/04 Citaton for 'Captain Reno'.*
http://www.bloembollenvisie.nl/laatstenieuws/2005/08/2005–08–29.htm.*

* cited by examiner

*Primary Examiner*—Kent Bell
*Assistant Examiner*—W. C. Haas
(74) *Attorney, Agent, or Firm*—Mark P. Bourgeois

(57) ABSTRACT

A new cultivar of *Zantedeschia* plant named 'Captain Reno' that is characterized by green leaves with light spots and purple violet colored flowers.

1 Drawing Sheet

Botanical classification: *Zantedeschia Spreng.*
Variety denomination: 'Captain Reno'.

BACKGROUND OF THE INVENTION

The present invention relates to a new and distinct cultivar of *Zantedeschia* plant botanically known as *Zantedeschia Spreng.* and hereinafter referred to by the cultivar name 'Captain Reno'.

'Captain Reno' is a hybrid that originated from the induced hybridization of the female or seed parent *Zantedeschia Spreng.* 'Zaailing 60' (not patented) and the male or pollen parent *Zantedeschia Spreng.* 'Zaailing 35' (not patented). The cultivar 'Captain Reno' was selected by the inventor in June of 2001 as a single plant within the progeny of the stated cross in Breezand, The Netherlands.

Asexual reproduction by tissue culture of the new cultivar 'Captain Reno' was first performed in November of 2001 in De Goorn, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Zantedeschia* cultivar 'Captain Reno'.

1. *Zantedeschia* 'Captain Reno' exhibits green leaves with light spots.
2. *Zantedeschia* 'Captain Reno' exhibits purple violet colored flowers.
3. *Zantedeschia* 'Captain Reno' exhibits strong flowers.

The closest comparison cultivar is *Zantedeschia* 'Galaxy' (unpatented). The new cultivar 'Captain Reno' is distinguishable from 'Galaxy' by the following characteristics:

1. 'Captain Reno' has a flower shape that is more round than the flower shape of 'Galaxy'.
2. 'Captain Reno' has darker flowers than 'Galaxy'.
3. 'Captain Reno' has darker leaves than 'Galaxy'.
4. 'Captain Reno' has a leaf shape that is more round than the leaf of 'Galaxy'.
5. 'Captain Reno' has larger flowers than 'Galaxy'.

The new cultivar 'Captain Reno' is distinguishable from the male parent *Zantedeschia* 'Zaailing 35' in having a smaller overall size. The new cultivar 'Captain Reno' is distinguishable from the female parent *Zantedeschia* 'Zaailing 60' in having purple violet flowers. 'Zaailing 60' has pink flowers.

BRIEF DESCRIPTION OF THE DRAWING

The accompanying photograph illustrates the distinguishing traits of *Zantedeschia* 'Captain Reno'. The plant in the photograph shows an overall view of a 24 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Zantedeschia* cultivar named 'Captain Reno'. Data was collected in Boskoop, The Netherlands from 24 month old greenhouse grown plants in 17 cm. containers. The time of year was Winter and the average temperature was 24 degrees Centigrade during the day and 17 degrees Centigrade at night. No photoperiodic treatments were used. Gibberellic Acid was used to induce flowering. Color determinations are in accordance with The Royal Horticultural Society Colour Chart 2001 edition, except where general color terms of ordinary dictionary significance are used. The growing requirements are similar to the species. 'Captain Reno' has not been tested under all possible conditions and phenotypic differences may be observed with variations in environmental, climatic, and cultural conditions, however, without any variance in genotype.

Botanical classification: *Zantedeschia Spreng.* 'Captain Reno'.
Use: Ornamental.
Parentage: 'Captain Reno' is a hybrid plant that resulted from the induced hybridization of the following parent plants:
*Female parent.*—*Zantedeschia Spreng.* 'Zaailing 60'.
*Male parent.*—*Zantedeschia Spreng* 'Zaailing 35'.
Vigor: Moderate.
Growth rate: Moderate.
Growth habit: Free branching from base.
Plant shape: Globose.
Suitable container size: 14 cm diameter container.
Height: Average 29 cm to top of leaf plane, 29 cm to top of inflorescences.
Width: Average 42 cm. in width.
Hardiness: USDA Zone 10.
Propagation: Tissue Culture.
Time to initiate roots: Approximately 540 days to produce roots on an initial cutting at between 17 and 25 degrees Centigrade.
Crop time: 720 days.
Root system: Fine and fibrous.
Stem: No stems, Leaves grow directly from base, Average 10 clumps.
Foliage:
*Texture.*—Smooth, slightly leathery.
*Leaf arrangement.*—Alternate, growing from the base.
*Compound or single.*—Single.
*Leaf shape.*—Lanceolate.
*Leaf apex.*—Acute.
*Leaf base.*—Long attenuate.
*Leaf texture.*—Smooth and leathery.
*Leaf length.*—Average 14.4 cm in length.
*Leaf width.*—5 cm in width.
*Quantity of leaves per clump.*—Average 4.
*Pubescence.*—Absent.
*Leaf margin.*—Entire, wavy, lower half wavier than upper halves.
*Vein pattern.*—Pinnate.
*Young leaf color* (*upper surface*).—143A, with small chronic, occasional dots 145D.
*Young leaf color* (*lower surface*).—143A to 144A, with occasional dots 145D.
*Mature leaf color* (*upper surface*).—137A, with sparse dots of 157D.
*Mature leaf color* (*lower surface*).—137A, with sparse dots of 157D.
*Vein color* (*lower surface*).—144B.
*Vein color* (*upper surface*).—143A.
*Leaf attachment.*—Petiolate.
*Petiole dimensions.*—Average 18.2 cm in length, 3 mm in diameter at distal end, 6 mm in diameter at proxil end, 5 mm in height.
*Petiole aspect.*—Round.
*Petiole texture.*—Smooth.
*Petiole surface.*—Slightly glossy.
*Petiole color.*—144B with a base 145C.
*Petiole sheath dimensions.*—Average 5.7 cm in length and 4 mm in diameter.
*Petiole sheath color.*—145C to 145D.
*Durability of foliage to stress.*—Moderate to high.
Inflorescence:
*Inflorescence arrangement.*—Spathes with spadices held beyond the foliage.
*Flowering habit.*—Continuous.
*Quantity of spathes per plant.*—10.
*Natural flowering season.*—Autumn to early spring.
*Time to flower or response time.*—8 months.
*Fragrance.*—Absent.
*Self-cleaning or persistent.*—Persistent.
*Flower longevity.*—Lasts approximately 2 months on plant.
*Spathe aspect.*—Concave, strongly cupped with a wavy margin, spadices columnar, slightly tapering toward the top.
*Spathe dimensions.*—Average 7.7 cm in length, 4.9 cm in width and 7.7 cm in height.
*Spathe texture.*—Glabrous, slightly leathery.
*Spathe shape.*—Broad ovate.
*Spathe margin.*—Entire, wavy.
*Spathe apex.*—Mucronate.
*Spathe base.*—Cuneate.
*Spathe color when opening* (*front side*).—N79A.
*Spathe color when opening* (*back side*).—N77A to N79A, base 146B.
*Spathe color when fully opened* (*front side*).—N79A, base N77B.
*Spathe color when fully opened* (*back side*).—N79B with irregular stripes and blotches 85D.
*Spathe color fading to.*—N77B to N79B, rear side base 143A to 143B.
*Spadix shape.*—Columnar.
*Spadix tip.*—Obtuse.
*Spadix base.*—Obtuse.
*Spadix dimensions.*—Average 2.9 cm in length and 5.5 mm in diameter.
*Spadix color when opening* (*upper area*).—4C.
*Spadix color when opening* (*lower area*).—157D.
*Spadix color when fully opened* (*upper area*).—13B.
*Spadix color when fully opened* (*lower area*).—157D.
*Quantity of flowers per spadix.*—Average pistilate flowers 27, staminate flowers 350.
*Spadix flower shape.*—Pistilate flowers rounded, staminate flowers irregular, narrow oblong.
*Spadix flower dimensions.*—Pistilate flowers 2 mm in diameter and 1.5 mm in depth, staminate flowers 1 mm in diameter and 0.5 mm in depth.
Reproductive organs:
*Anther color.*—13C.
*Amount of pollen.*—Low.
*Pollen color.*—8D.
*Stigma color.*—11B.
*Ovary color.*—155A.
Peduncle:
*Peduncle dimensions.*—Average 23.8 cm in length and 5 mm in diameter.
*Peduncle angle.*—20°.
*Peduncle color.*—145A, lighter at the base 145D.
*Peduncle strength.*—Moderate.
Seed: Seed production has not been observed.
Disease and insect resistance: Plants of the new *Zantedeschia* have not been observed for disease or insect resistance.

It is claimed:

1. A new and distinct variety of *Zantedeschia* plant named 'Captain Reno' as described and illustrated.

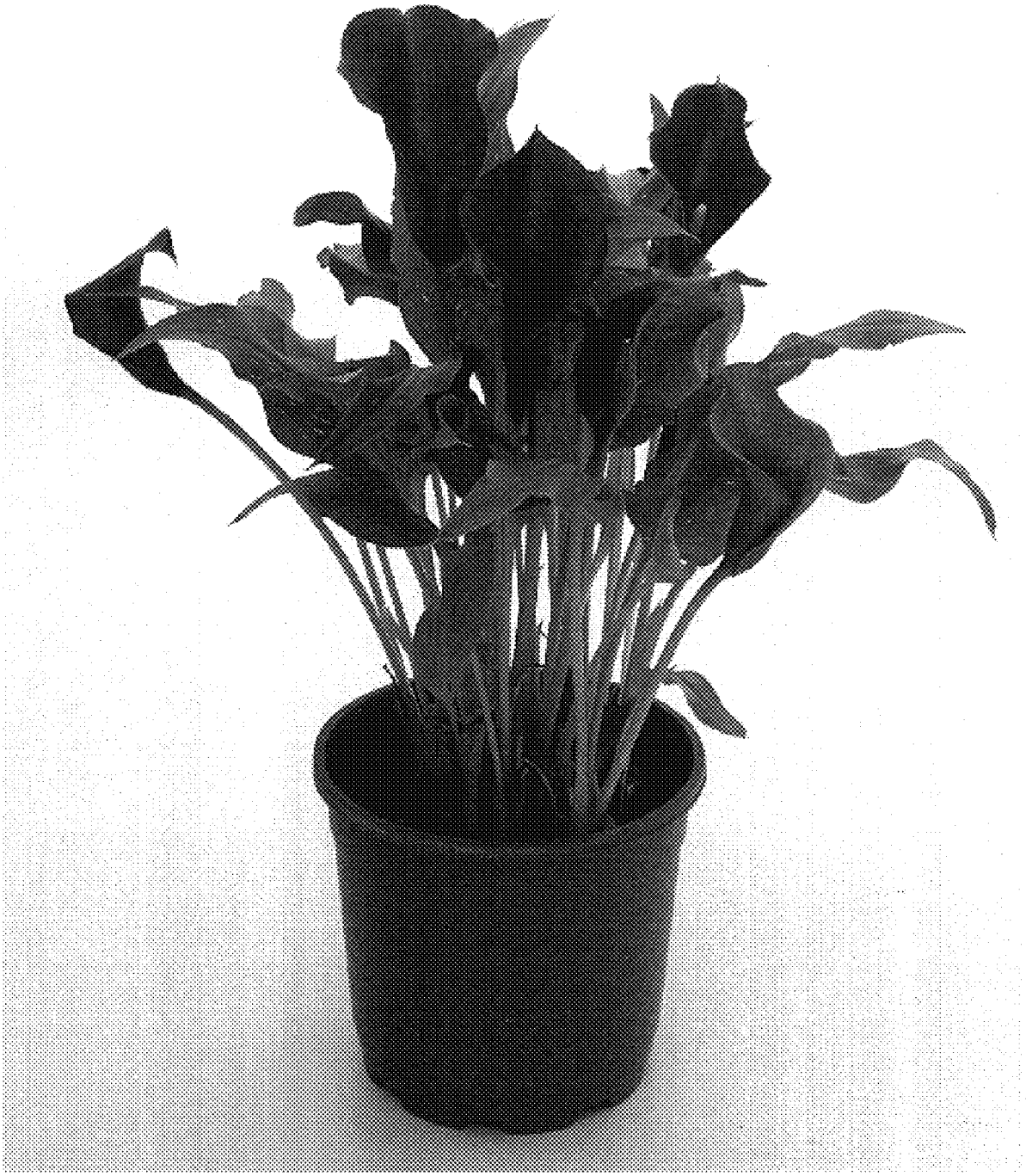

* * * * *